United States Patent
Bencini

(10) Patent No.: US 6,579,278 B1
(45) Date of Patent: *Jun. 17, 2003

(54) BI-DIRECTIONAL STEERABLE CATHETER WITH ASYMMETRIC FULCRUM

(75) Inventor: Robert F. Bencini, Sunnyvale, CA (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/566,175

(22) Filed: May 5, 2000

(51) Int. Cl.⁷ ............................................. A61M 25/098
(52) U.S. Cl. ...................................... 604/528; 600/585
(58) Field of Search ................................ 604/528, 523; 600/585, 433, 434, 435

(56) References Cited

U.S. PATENT DOCUMENTS

| | | | |
|---|---|---|---|
| 5,273,535 A | 12/1993 | Edwards et al. | 604/95 |
| 5,328,467 A * | 7/1994 | Edwards et al. | 600/373 |
| 5,358,478 A | 10/1994 | Thompson et al. | 604/95 |
| 5,395,327 A | 3/1995 | Lundquist et al. | |
| 5,397,321 A | 3/1995 | Houser et al. | |
| 5,656,029 A * | 8/1997 | Imran et al. | 604/528 |
| 5,797,842 A * | 8/1998 | Pumares et al. | 600/435 |
| 5,820,591 A * | 10/1998 | Thompson et al. | 604/529 |
| 5,885,288 A | 3/1999 | Aust et al. | |
| 5,906,590 A | 5/1999 | Hunjan et al. | 604/95 |
| 6,074,351 A * | 6/2000 | Houser et al. | 600/585 |
| 6,198,974 B1 * | 3/2001 | Webster, Jr. | 600/146 |

FOREIGN PATENT DOCUMENTS

WO    WO 94/11057    5/1994

* cited by examiner

*Primary Examiner*—Brian L. Casler
*Assistant Examiner*—Mark Han
(74) *Attorney, Agent, or Firm*—Bingham McCutchen LLP

(57) ABSTRACT

A steerable medical device comprises an elongated tubular body and first and second stiffening members, preferably in the form of compression coils or flat flexible wires. The stiffening members are arranged such that when a user engages a steering assembly, incorporated into the device, a distal end of the tubular body can be selectively bent in a first direction into a first configuration or in a second direction into a second configuration. The first and second configurations are functions of the lengths and locations of the first and second stiffening members.

48 Claims, 9 Drawing Sheets

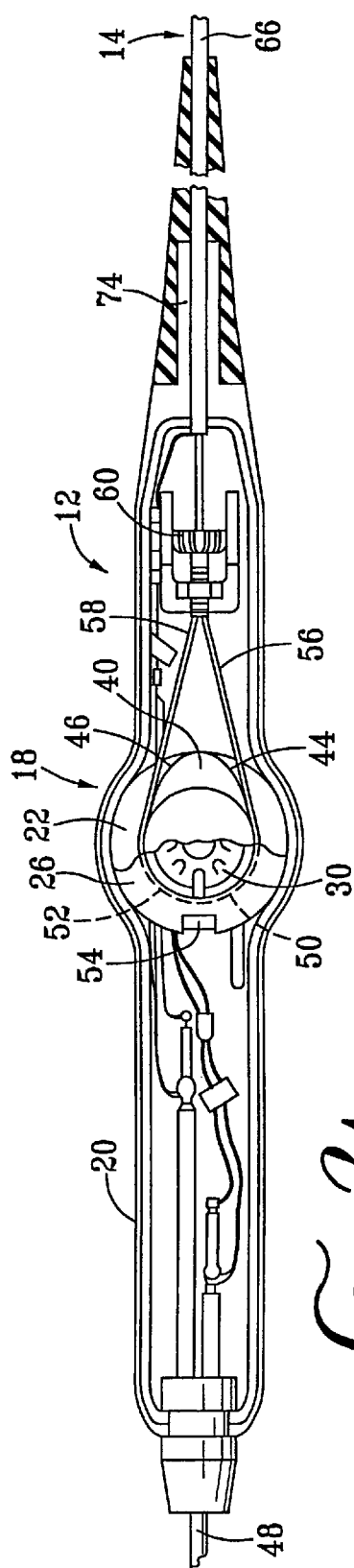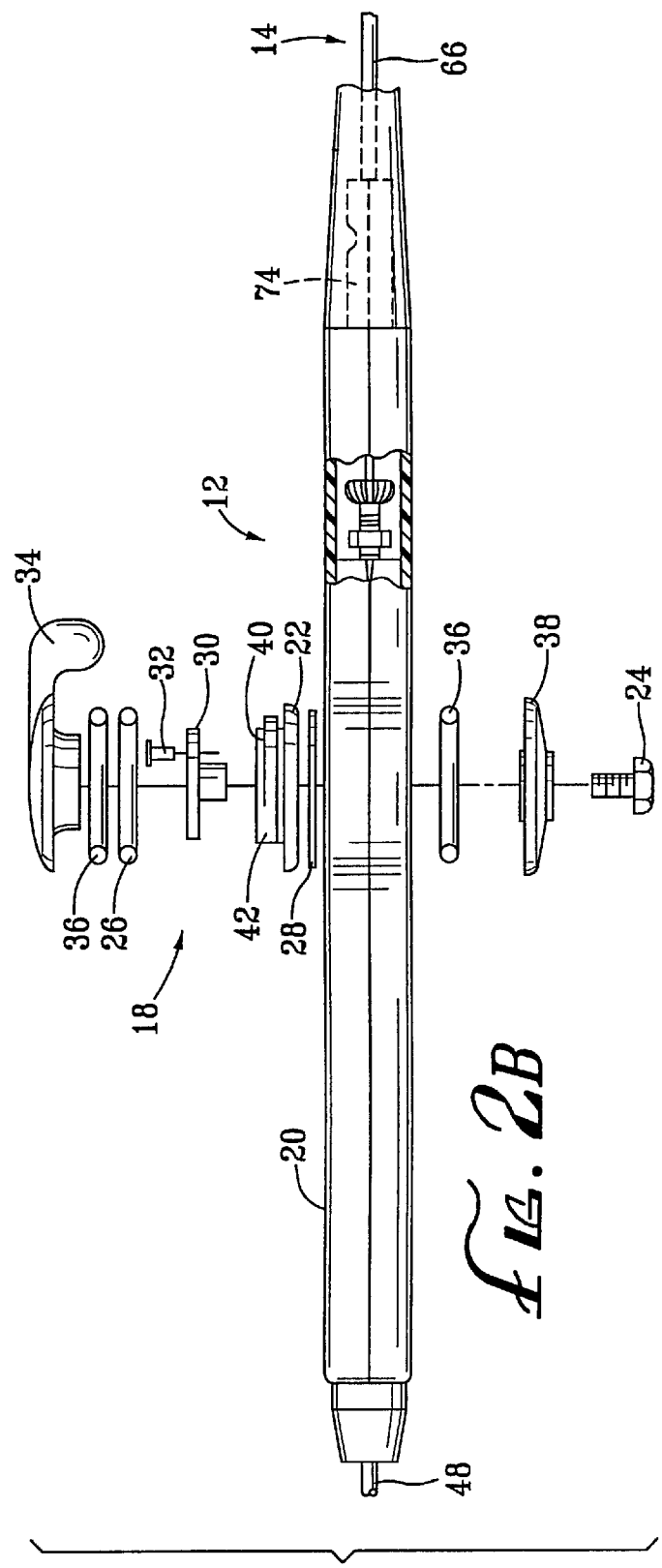

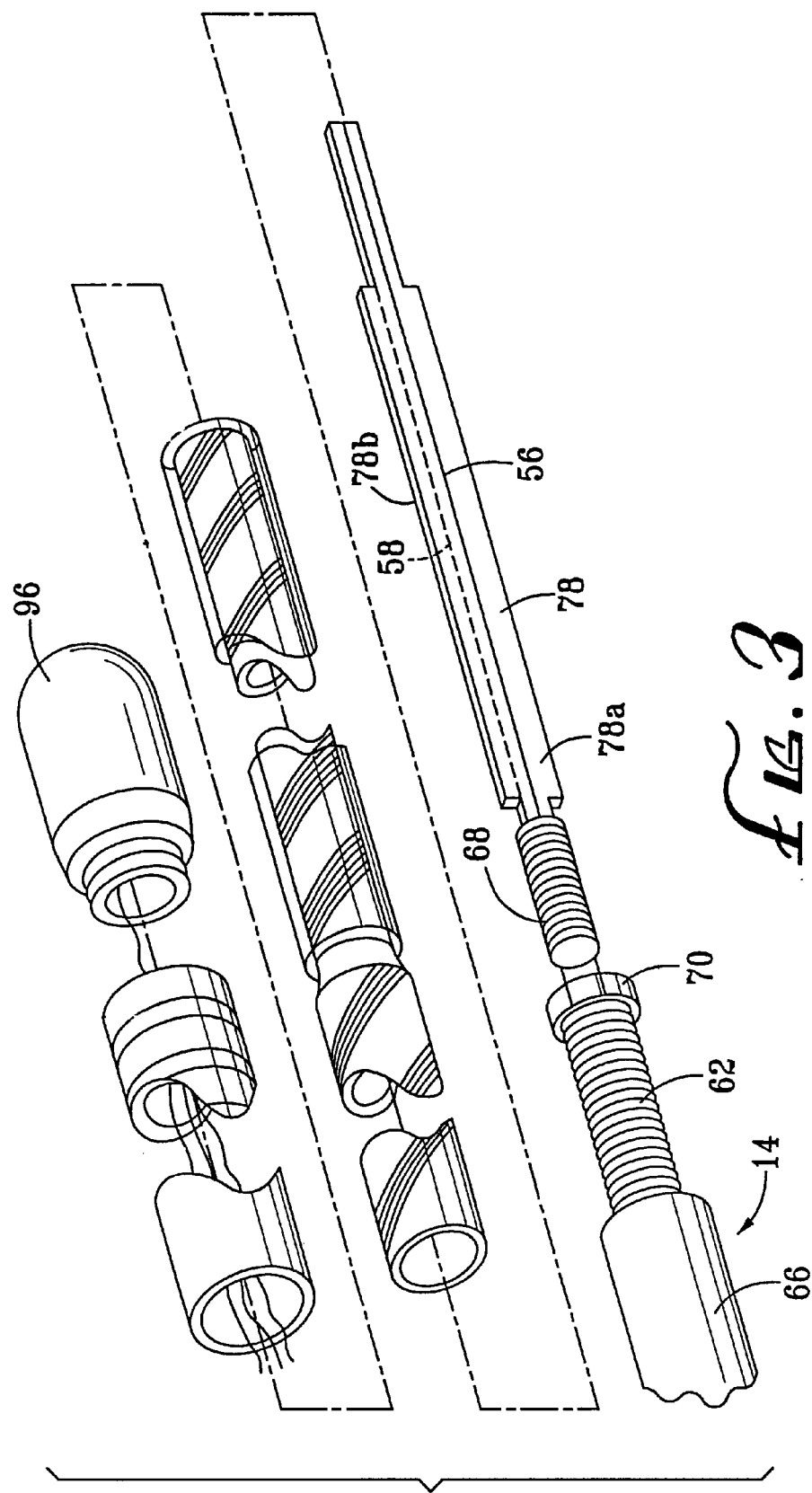

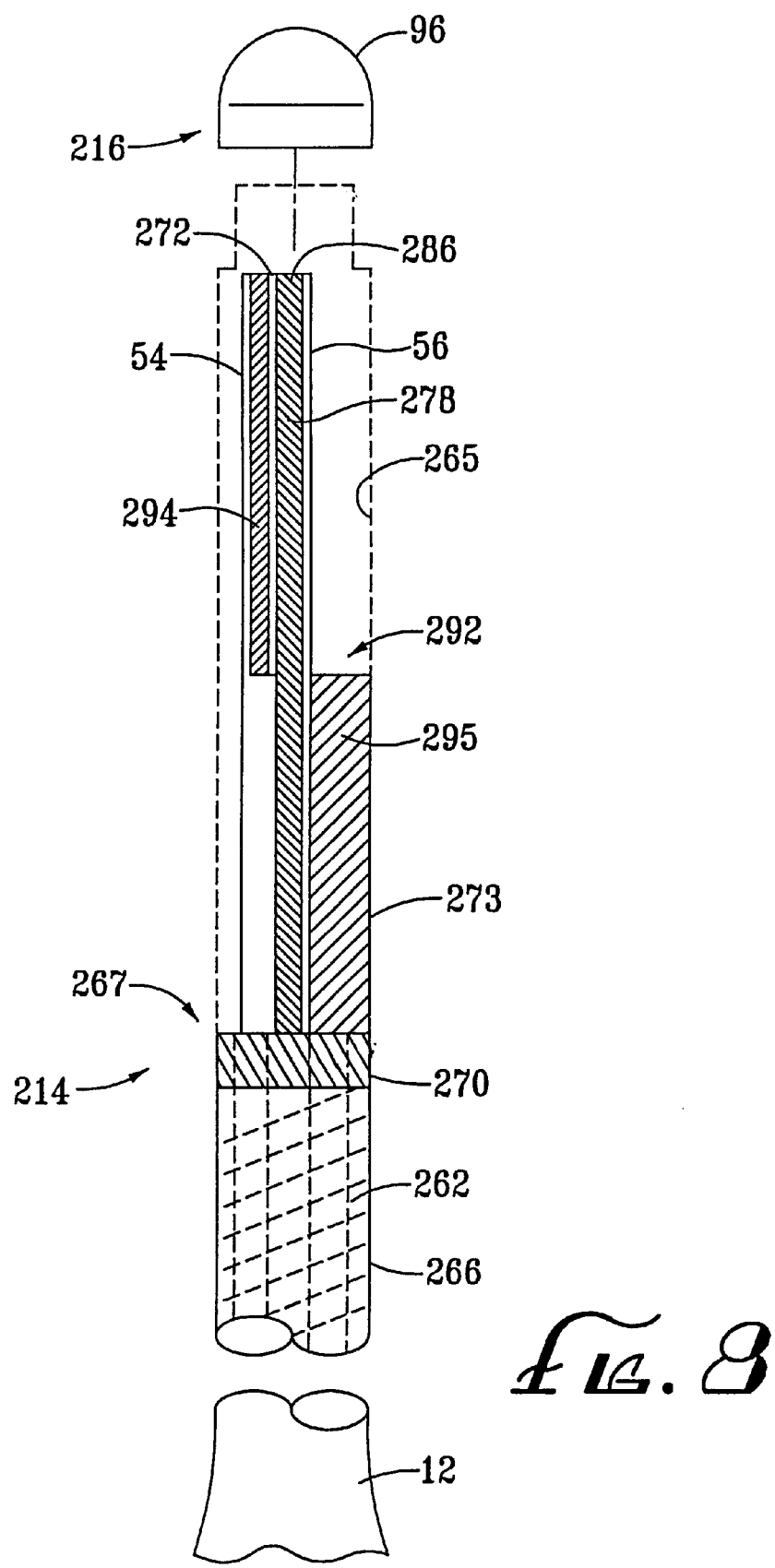

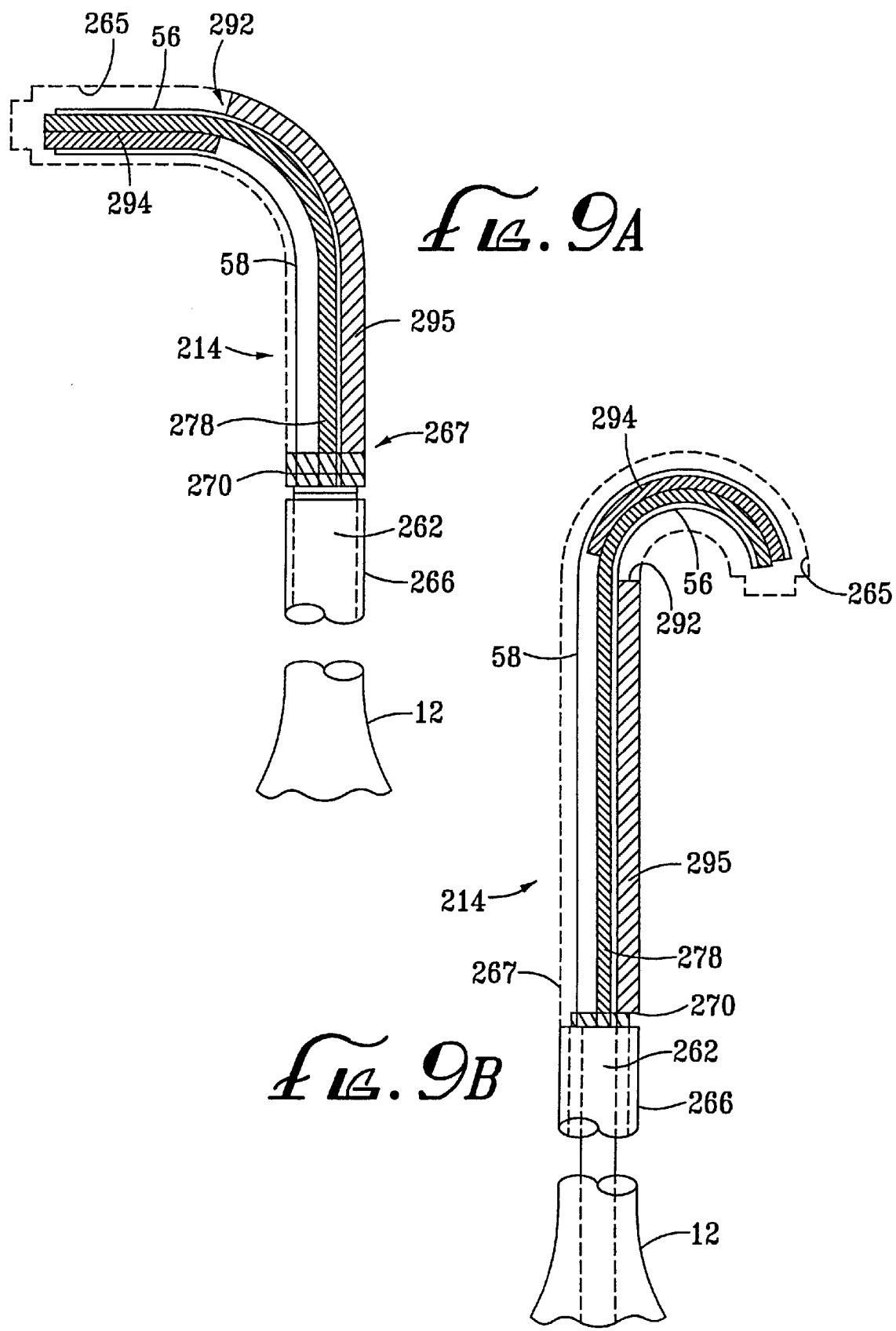

BI-DIRECTIONAL STEERABLE CATHETER WITH ASYMMETRIC FULCRUM

FIELD OF THE INVENTION

This invention relates to catheters and more particularly to steering mechanisms that allow the catheters to be guided through the blood vessels of a patient.

BACKGROUND OF THE INVENTION

Physicians make widespread use of catheters in medical procedures to gain access into interior regions of the body. It is important that the physician can control carefully and precisely the movement of the catheter within the body, especially during procedures that ablate tissue within the heart. These procedures, called electrophysiological therapy, are becoming more widespread for treating cardiac rhythm disturbances.

During these procedures, a physician steers a catheter through a main vein or artery (which is typically the femoral artery) into the interior region of the heart. The physician then further manipulates a steering mechanism to place the electrode carried in the tip of the catheter into direct contact with the tissue that is to be ablated. The physician directs radio frequency energy into the electrode tip to ablate the tissue and form a lesion.

Since the heart is formed from several asymmetrically shaped chambers, cardiac ablation especially requires the ability to precisely bend and shape the tip end of the catheter to position the ablation electrode within the heart.

SUMMARY OF THE INVENTION

A steerable medical device constructed in accordance with the present invention comprises an elongate tubular body having a proximal end and a distal end. The tubular body has a first stiffening member with a distal end that extends from the tubular body proximal end to a first point on the tubular body, and a second stiffening member extending from a second point on the tubular body to a third point on the tubular body.

The second point on the tubular body may be distal to the first point and may also be the distal end of the first stiffening member. Preferably, the first and second stiffening members are formed from compression coils.

The tubular body may further comprise a center support wire and the steerable medical device may further comprise a steering assembly and a first and second steering wire for selectively bending the tubular body in a first direction into a first configuration and in a second direction into a second configuration. The first and second configurations are preferably functions of the lengths of the respective stiffening members.

In an alternate embodiment, a steerable medical device constructed in accordance with the present invention comprises an elongated tubular body with proximal and distal ends. The tubular body comprises a flexible sheath, which defines a lumen, having an inside surface and an outside surface, a first stiffening member extending from the tubular body to a first point on the tubular body, and a second stiffening member extending from a second point on the tubular body to a third point on the tubular body. The second stiffening member is attached to the inside surface of the sheath. Additionally, the steerable medical device may further comprise a center support wire extending from a distal end of the first stiffening member and a third stiffening member extending from a fourth point on the tubular body.

In a further embodiment, a steerable medical device constructed in accordance with the present invention comprises an elongated tubular body with a proximal end and a distal end. The tubular body comprises a flexible sheath with an inside surface and an outside surface, wherein the sheath defines a lumen, a center support wire extending through the lumen, a first stiffening member extending from a first intermediate point on the tubular body to a second intermediate point on the tubular body, a second stiffening member extending from a third intermediate point on the tubular body to a fourth intermediate point on the tubular body, wherein the first stiffening member is attached to the inside surface of the sheath and the second stiffening member is attached to the center support wire.

BRIEF DESCRIPTION OF THE DRAWINGS

FIG. 2A is a top cross-sectional view of a catheter handle assembly included in the steerable medical device of FIG. 1;

FIG. 2B is an exploded side view of the catheter handle assembly of FIG. 2A;

FIG. 3 is an exploded perspective view of a catheter guide tube assembly;

FIG. 8 is a side cross-sectional view of a third embodiment of a catheter guide tube assembly constructed in accordance with the present invention; and FIGS. 9A and 9B are diagrammatic views of the catheter guide tube assembly of FIG. 8 while being steered in left and right directions, respectfully.

DETAILED DESCRIPTION OF THE PREFERRED EMBODIMENTS

Figure 1:
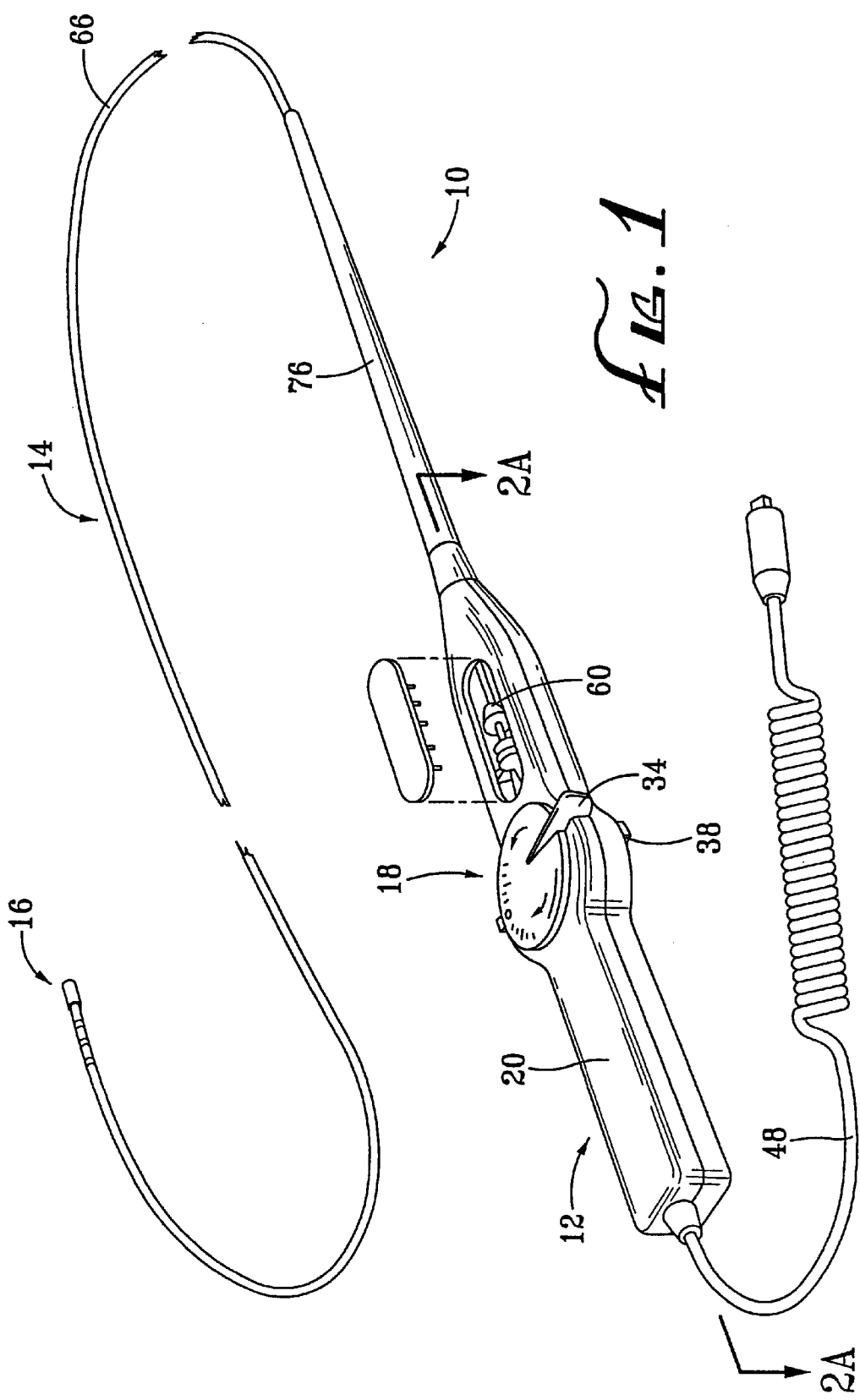
FIG. 1 is a perspective view of a steerable medical device constructed in accordance with the present invention.

FIG. 1 shows the assembly of a steerable medical device 10 constructed in accordance with the present invention. The medical device 10 includes three main assemblies: a handle assembly 12, a guide tube assembly 14, and an electrode tip assembly 16.

The medical device 10 is preferably a catheter, and can be used in various environments, for example, it may be used to provide electrophysiologic therapy in the interior regions of the heart. When used for this purpose, a physician grasps the handle assembly 12 and steers the guide tube assembly 14 through a main vein or artery (typically the femoral arterial) and into the interior region of the heart that is to be treated. By manipulating a steering mechanism 18 on the handle assembly 12, a physician can place the electrode tip assembly 16 in contact with the specific tissue that is to be ablated. Radio frequency energy is directed into the electrode tip assembly 16 to ablate the tissue it is in contact with.

As FIGS. 2A and 2B best show, the handle assembly 12 includes a housing 20 that encloses the steering mechanism 18. In a preferred embodiment, the steering mechanism 18 includes a rotating cam wheel 22 carried on a screw 24 within the housing 20. The cam wheel 22 is seated for rotation between a top washer 26 and a bottom washer 28. A lock nut 30 and a pin 32 couple an external steering lever 34 to the top of the cam wheel 22. The steering lever 34 seats against an O-ring 36.

Movement of the steering lever 34 by a user rotates the cam wheel 22 about the screw 24 within the housing 20. Clockwise movement of the steering lever 34 rotates the cam wheel 22 to the right. Counterclockwise movement of the steering wheel rotates the cam wheel 22 to the left. Contact between the steering lever 34 and the side of the housing 20 physically limits the range of left and right rotation of the cam wheel 22 within the housing 20. The steering mechanism 18 also includes an external locking lever 38 that an adhesive couples to the head of the screw 24. The locking lever 38 seats against another O-ring 36.

Movement of the locking lever 38 rotates the screw 24. Clockwise rotation of the locking lever 38 tightens the screw 24 to increase the seating force between the cam wheel 22 and the bottom washer 28. When moved fully clockwise into contact against the housing 20, the locking lever 38 imposes a seating force that prevents rotation of the cam wheel 22 by the steering lever 34. Counterclockwise movement of the locking lever 34 loosens the screw 24 to decrease the seating force and free the cam wheel 22 for rotation.

The cam wheel 22 includes a forward cam face 40 and a rear cam face 42. The forward cam face 40 is oriented toward the front of the housing 20, where the guide tube assembly 14 attaches. The forward cam face includes a right side surface 44 and a left side surface 46. The rear cam face 42 is oriented toward the back of the housing 20, where a coaxial cable 48 attaches. The rear cam face includes right and left side surfaces 50 and 52.

The cam wheel 22 also carries a wire fastener 54 between the right and left side surfaces 50 and 52 of the rear cam face 42. The wire fastener 54 holds the proximal ends of right and left catheter steering wires 56 and 58, which are soldered to the interior of the fastener 54.

The steering wires 56 and 58 extend from the opposite ends of the fastener 54 and along the associated left and right side surfaces 44/46 and 50/52 of the front and rear cam faces 40 and 42. The steering wires exit from a front portion of the housing 20 through the interior bore of a tension screw assembly 60. The distal ends of each of the steering wires 56 and 58 are attached to the electrode tip assembly 16.

The wire fastener 54, in association with the cam faces 40 and 42, translate rotation of the cam wheel 22 into lateral pulling movement of the steering wires 56 and 58 attached to a portion of the electrode tip assembly 16.

By rotating the cam wheel 22 to the left (i.e., by moving the steering lever 34 counterclockwise), the left steering wire 58 bears against the left front and rear cam surfaces 46 and 52. The cam surfaces 46 and 52 tension the left steering wire 58 to impose a discrete, constant pulling force that causes the electrode tip assembly 16 to bend to the left. Similarly, by rotating the cam wheel 22 to the right (i.e., by moving the steering lever 34 clockwise), the right steering wire 56 bears against the right front and rear cam surfaces 44 and 50. The cam surfaces 44 and 50 tension the right steering wire 56 to impose a discrete, constant pulling force that causes the electrode tip assembly 16 to bend to the right.

Rotation of the tension screw assembly 60 additionally varies the amount of slack (i.e., tension) in the steering wires 56 and 58 between the wire fastener 54 and the distal ends of the steering wires 56 and 58. This controls the responsiveness of the electrode tip assembly 16 to a specific angular rotation of the cam wheel 22.

The component parts of the handle assembly 12 can be constructed from various materials, depending upon the durability needed and the sterilization process used. For example, when EtO sterilization is used, the housing 20 and bottom washer 28 can be made of a polycarbonate material. In this arrangement, the cam wheel 22, steering lever 34, and locking lever 38 can be made of a delrin material. These plastic materials are durable and EtO sterilizable. In this assembly, the lock nut 30, pin 32, and screw 24 are preferably made of a metallic material like brass or stainless steel.

Further details of a preferred embodiment of the handle assembly 12 and the electrode tip assembly 16 are found in U.S. Pat. Nos. 5,358,478 and 5,906,590, the details of which are hereby incorporated by reference into the present application.

A steerable medical device 10 constructed in accordance with the present invention allows a user to selectively bend the distal portion of the guide tube assembly 14, and more specifically, the electrode tip assembly 16, in two directions, each bending direction having its own specific configuration. For instance, by steering the catheter to the right, the electrode tip assembly 16 bends to the right and into a first configuration, e.g. a substantially curved profile with a first predetermined circumference. By steering the catheter to the left, the electrode tip assembly 16 bends to the left and into a second configuration, e.g. a substantially curved profile with a second predetermined circumference. The specific circumference and shape that the electrode tip assembly 16 will assume is related to the size, shape, material of construction, and location of various stiffening members located along the guide tube assembly 14. Notably, the shape that the electrode tip assembly assumes is not restricted to a completely curved profile and it may include sections that are substantially straight.

Figure 4:
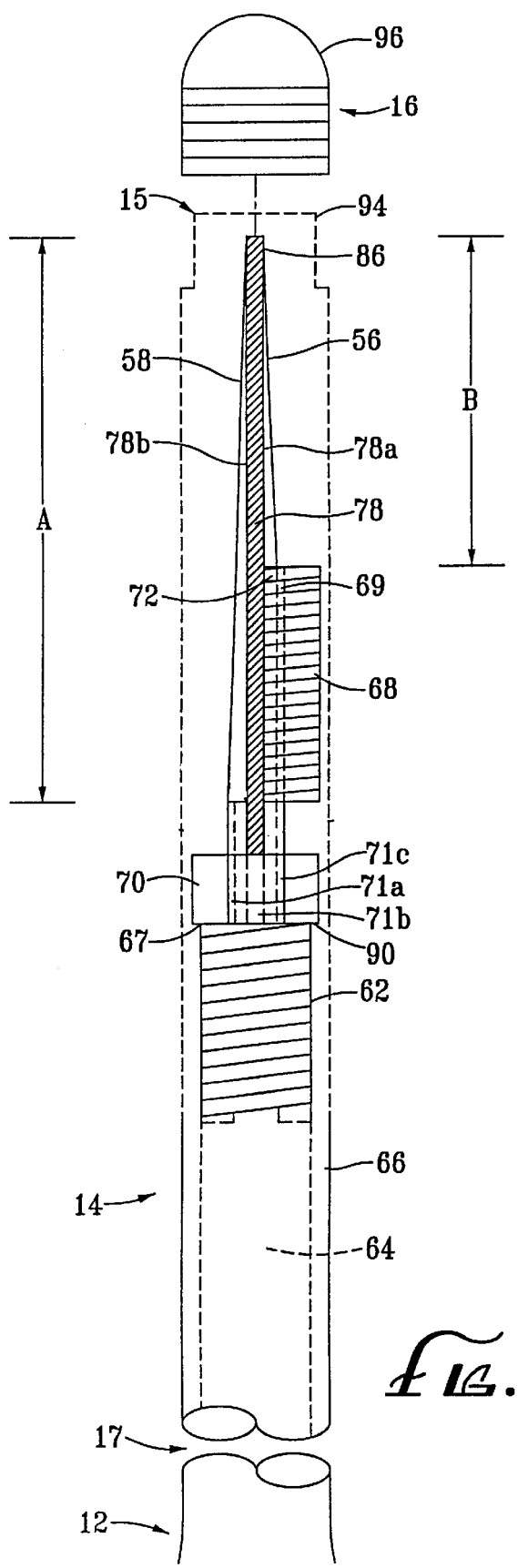
FIG. 4 is a side cross-sectional view of the catheter guide tube assembly of FIG. 3.

FIGS. 3 and 4 show, in greater detail, a preferred embodiment of the guide tube assembly 14 of a steerable medical device constructed in accordance with the present invention. The guide tube assembly 14 has a generally tubular body with a proximal end 17 connected to the handle assembly 12, and a distal end 15 that engages with the electrode tip assembly 16. In FIGS. 3 and 4, an electrode 96 is shown located on very distal end of the electrode tip assembly 16. Circumferetial electrodes (not shown) may also be included on the electrode tip assembly 16. The guide tube assembly 14 includes a flexible shaft 62, preferably in the form of a compression coil, that extends from the handle assembly 12 to a first intermediate point 90 along the length of the guide tube assembly 16. The shaft 62 encloses an interior bore 64 through which various components of the steerable medical device pass. For example, each of the steering wires 56 and 58 are attached to the steering assembly 18 and pass through the length of the interior bore 64 of the shaft 62. Conducting wires (not shown) that supply power to the electrodes are also enclosed within the interior bore 64 of the shaft 62.

The shaft 62 may be constructed in various ways. In the embodiment shown in FIGS. 3 and 4, the shaft 62 is a compression coil and comprises a length of stainless steel coiled into a flexible spring. A sheath 66 of extruded plastic material containing wire braids encloses the shaft 62. The sheath 66 is preferably made from a bio-compatible, thermoplastic material, such as polyurethane, a polyolefin or polyetherpolyamide block copolymer, and extends the entire length of the tube assembly 14 and electrode tip assembly 16.

The guide tube assembly 14 can be made in various lengths. In the case of cardiac ablation catheters, the guide tube assembly 14 is usually about 100 centimeters long. Shorter or longer lengths may be provided in order to facilitate various other medical procedures.

The shaft 62 forms a first stiffening member for the steerable medical device. A center support wire 78 extends from a distal end 67 of the shaft 62. The center support wire 78 is a flexible and bendable support wire or spring, preferably made of stainless steel and having a generally flat profile with right 78a and left 78b surfaces.

The distal end of the left steering wire 58 is soldered or otherwise affixed to the left surface 78b of a distal end 86 of the center support wire 78. When pulled by left rotation of the rotatable cam 23, the left steering wire 58 is necessarily shortened, and causes the center support wire 78 to bend to the left. The distal end of the right steering wire 56 is soldered or otherwise affixed to the right surface 78a of the distal end 86 of the center support wire 78. When pulled by right rotation of the rotatable cam 23, the right steering wire 56 is necessarily shortened, and causes the center support wire 78 to bend to the right.

A guide tube connector 70 is engaged with the distal end 67 of the shaft 62. The guide tube connector 70 includes three apertures 71a, 71b, and 71c that allow the steering wires 56 and 58 and the center support wire 78 to extend from within the central bore 74, through the guide tube connector 70, and into the region of the guide tube assembly 14 that is distal to the guide tube connector 70.

Immediately distal to the guide tube connector 70, and in contact therewith, is a second stiffening member 68 extending from a second intermediate point to a third intermediate point on the guide tube assembly 16 as shown in FIG. 4. The second stiffening member 68 is also preferably a compression coil, similar in construction to the shaft 62. However, unlike the shaft 62, which forms the first stiffening member, the second stiffening member 68 is not substantially concentric with the sheath 66. Rather, the second stiffening member 68 is disposed on one side of the center support 78 and is substantially aligned with one of the steering wires. In FIGS. 3 and 4, the second stiffening member 68 is disposed on the right side of the center support wire 78 and is substantially aligned with the right steering wire 56. The second stiffening member 68 includes a passage 69 through which the right steering wire 56 extends. The application of a spot weld 72 fixes the distal end of the second stiffening member 68 to the right surface 78a of the center support 78. The proximal end of the second stiffening member 68 is connected to the guide tube connector 70.

With the arrangement shown in FIG. 4, the distal portion of the guide tube assembly 14, and more specifically, the electrode tip assembly 16, assumes a first shape when steered to the left and another shape when steered to the right. In operation, when the left steering wire 58 is pulled, i.e. by activation of the steering assembly 18, the center support wire 78 and therefore the distal portion of the guide tube assembly 14, including the electrode assembly 16, will deflect to the left. The guide tube assembly 16 will form a curve with a circumference substantially equal to the distance "A" shown in FIG. 4, namely, the distance between the point where the second stiffening member 68 is welded to the guide tube connector 70 and the distal end of the electrode tip assembly 16.

Figures 5A, 5B:
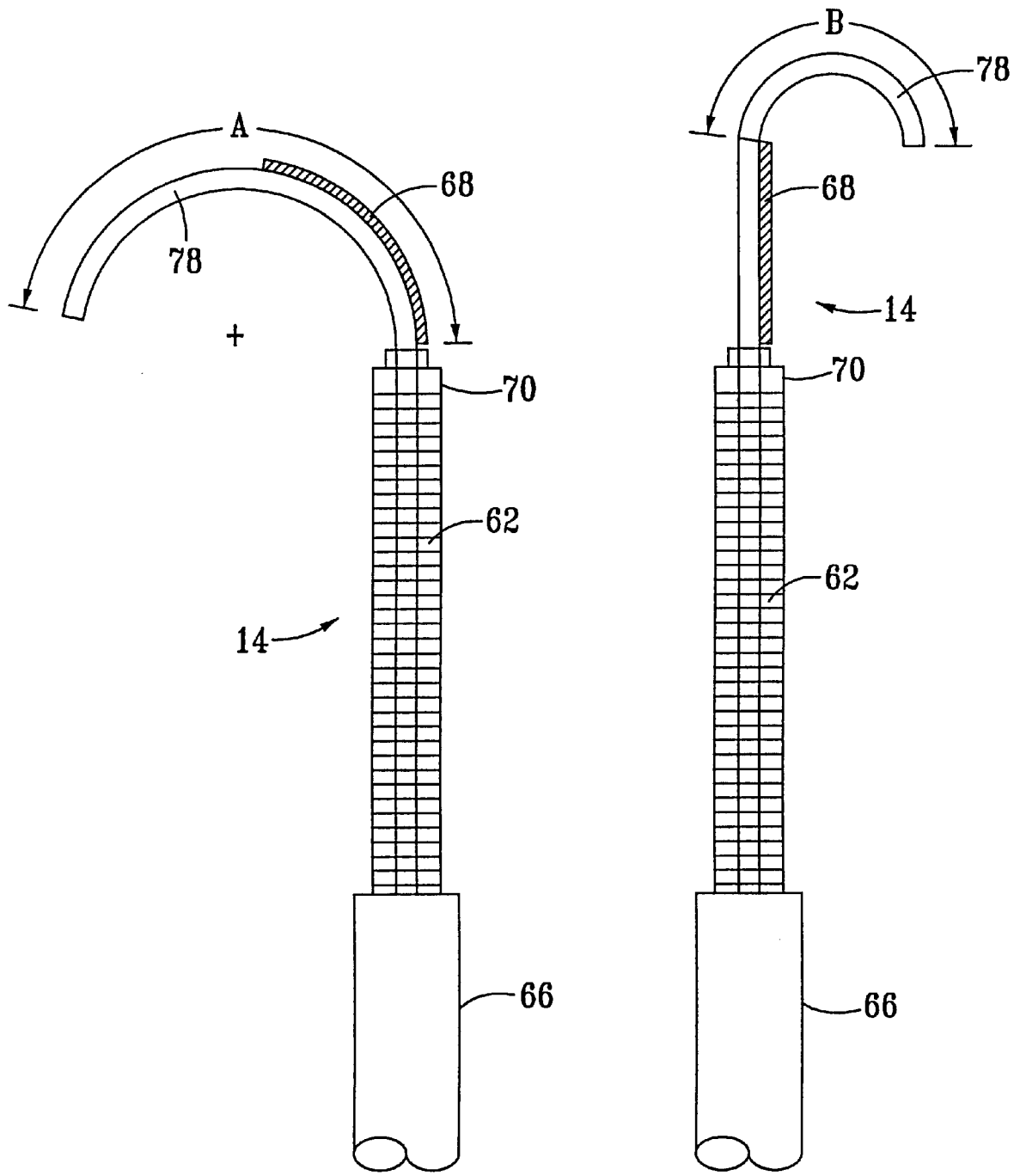
FIGS. 5A and 5B are diagrammatic views of the catheter guide tube assembly of FIG. 4 after being steered in left and right directions, respectfully.

FIGS. 5A and 5B show the resulting deflection of the distal region of the guide tube assembly 14 when the guide tube assembly 14 is steered to the left and right respectively.

When steered to the left (FIG. 5A), since the second stiffening member is attached to the center support wire 78, the second stiffening member 68 bends and extends and does not interfere with the subsequent deflection of the center support wire 78. In FIG. 5A, the fulcrum point of the bending moment is adjacent to the guide tube connector 70, therefore, the portion of the guide tube assembly 14 that is distal to the guide tube connector 70 is free to deflect. Thus, it can be appreciated that the steering mechanism 18, center support wire 78, and left steering wire 58 are arranged to selectively bend the guide tube assembly 14 in a first direction into a first configuration, as illustrated in FIG. 5A.

When pulled to the right (FIG. 5B), the second stiffening member 68 is already completely compressed and therefore forms a substantially rigid member. The second stiffening member 68 prevents the adjacent portion of the center support wire 78 and the adjacent portion of the guide tube assembly 16 from deflecting. Since the second stiffening member 68 is connected to the center support wire 78 at the spot weld 72, and is similarly connected to the guide tube connector 70, the fulcrum of the bending moment is at the distal end of the second stiffening member 68. Thus, only the portion of the guide tube assembly 16 that is distal to the second stiffening member 68, bends into a curve with a circumference substantially equal to the distance "B", namely, the distance between the distal end of the second stiffening member 68, and the distal end of the electrode tip assembly 16. Thus, it can be appreciated that the steering mechanism 18, center support wire 78, right steering wire 56, and second stiffening member 68 are arranged to selectively bend the guide tube assembly 14 in a second direction into a second configuration, as illustrated in FIG. 5B.

Figure 6:
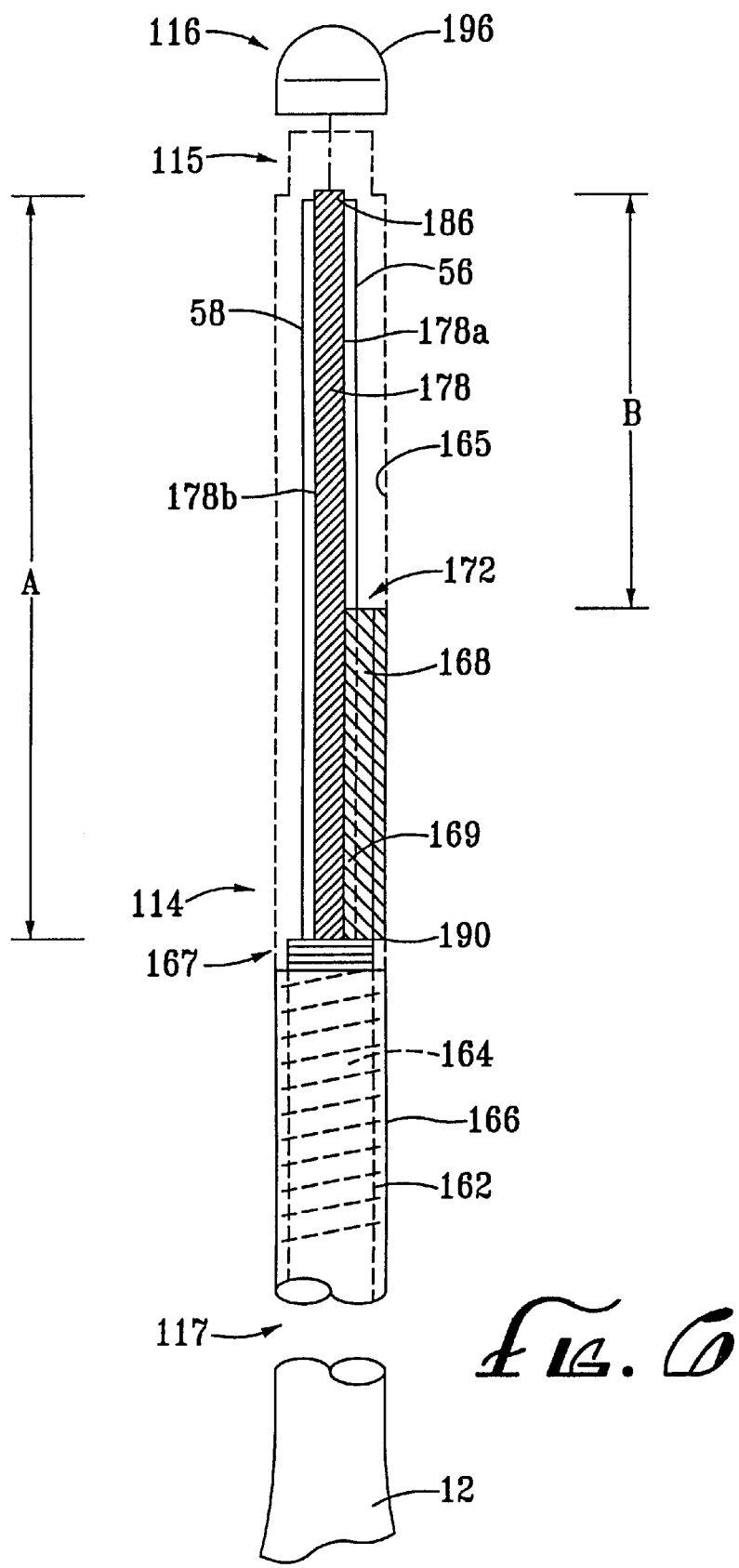
FIG. 6 is a side cross-sectional view of a second embodiment of a catheter guide tube assembly constructed in accordance with the present invention.
Figure 7A:
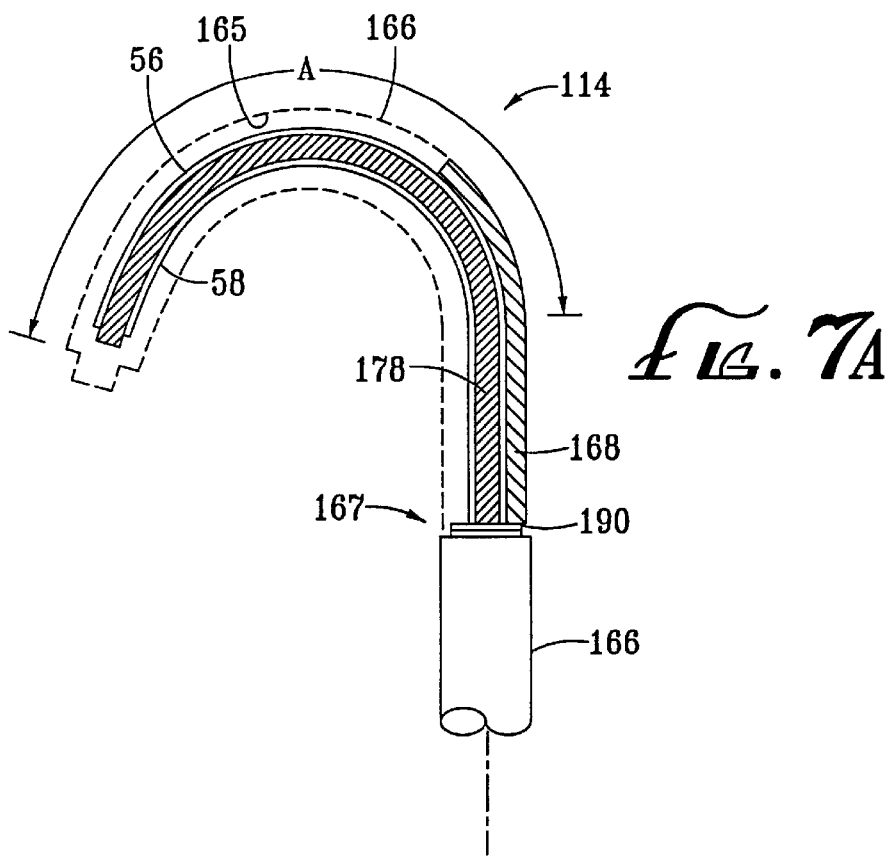
FIGS. 7A and 7B are diagrammatic views of the catheter guide tube assembly of FIG. 6 after being steered in left and right directions, respectfully.
Figure 7B:
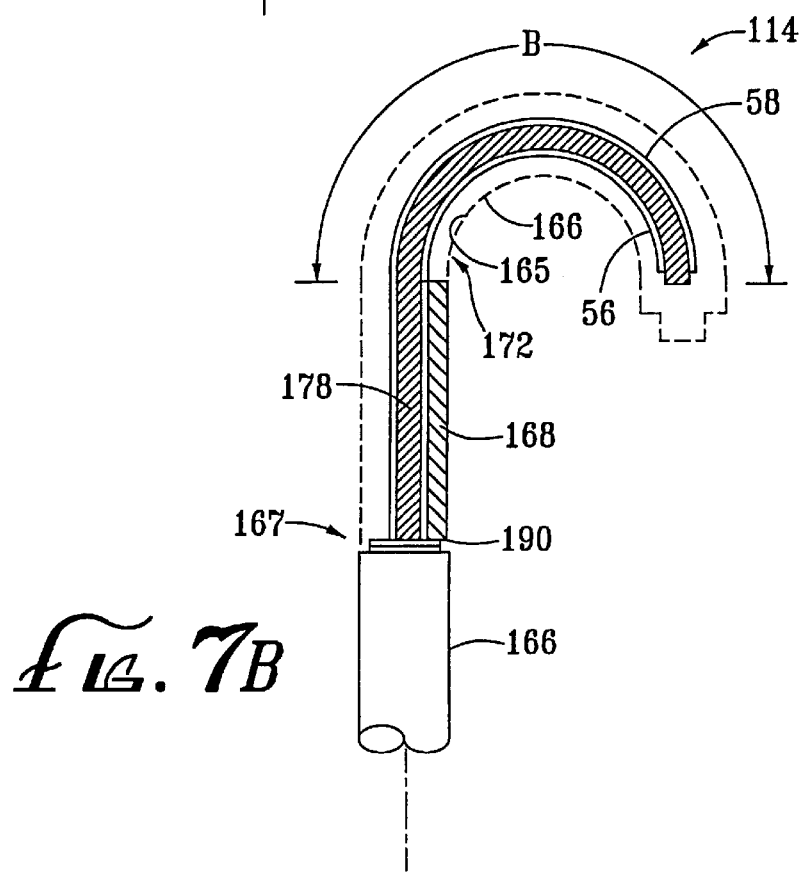

FIGS. 6–7B show an alternate embodiment of a guide tube assembly 114 constructed in accordance with the present invention. While generally similar in construction to the guide tube assembly 14 described previously, the guide tube assembly 114 utilizes a different configuration of stiffening members in order to enable its distal region to be steered into two different shapes.

The guide tube assembly 114 has a generally tubular body with a proximal end 117 connected to the handle assembly 12, and a distal end 115 that engages with an electrode tip assembly 116. An electrode 196 is located on the electrode tip assembly 116. The guide tube assembly 114 includes a flexible shaft 162, that extends from the handle assembly 12 to first intermediate point 190 along the length of the guide tube assembly 114. The shaft 162 encloses an interior bore 164 through which various components of the steerable medical device pass. For example, the steering wires 56 and 58 are attached to the steering assembly 18 and pass through the length of the guide tube assembly 114 through the interior bore 164 of the shaft 162. Conducting wires (not shown) that supply power to the electrodes are also enclosed within the interior bore 164 of the shaft 162.

The shaft 162 may be constructed in various ways. In the embodiment shown in FIG. 6, the shaft 162 is a compression coil and comprises a length of stainless steel coiled into a flexible spring. A sheath 166 of extruded plastic material containing wire braids encloses the shaft 162. The sheath 166 is preferably made from a bio-compatible, thermoplastic material, such as polyurethane, a polyolefin or polyether-polyamide block copolymer, and extends the entire length of the guide tube assembly 114 and electrode tip assembly 116.

The guide tube assembly 114 can be made in various lengths. In the case of cardiac ablation catheters, the guide tube assembly 114 is usually about 100 centimeters long.

Shorter or longer lengths may be provided in order to facilitate various other medical procedures.

The shaft 162 forms a first stiffening member for the steerable medical device. A center support wire 178 extends from a distal end 167 of the shaft 162. The center support wire 178 is a bendable and flexible support wire or spring, preferably made of stainless steel and having a generally flat profile with right 178a and left 178b surfaces.

The distal end of the left steering wire 58 is soldered or otherwise affixed to the left surface 178b of a distal end 186 of the center support wire 178. When pulled by left rotation of the rotatable cam 23, the left steering wire 58 is necessarily shortened, and causes the center support wire 178 to bend to the left. The distal end of the right steering wire 56 is soldered or otherwise affixed to the right surface 178a of the distal end 186 of the center support wire 178. When pulled by right rotation of the rotatable cam 23, the right steering wire 58 is necessarily shortened, and causes the center support wire 178 to bend to the right.

Immediately distal to the distal end 167 of the shaft 162, is a second stiffening member 168. The second stiffening member 168 is preferably the center support wire 178. The second stiffening member 168 is disposed on one side of the center support wire 178 and is substantially aligned with one of the left or right steering wires. In FIG. 6, the second stiffening member 168 is disposed on the right side of the center support wire 178 and is substantially aligned with the right steering wire 56. The second stiffening member 168 includes a passage 169 through which the right steering wire 56 extends. The second stiffening member 168 is affixed to an inside surface 165 of the sheath 166 but is not connected to the center support wire 178. The right steering wire 56 is free to move within the passage 169.

With the arrangement shown in FIG. 6, the distal portion of the guide tube assembly 114, and more specifically, the electrode tip assembly 116, assumes a first shape when steered to the left and another shape when steered to the right. In operation, when the left steering wire 58 is pulled, i.e. by activation of the steering assembly 18, the center support wire 178 and therefore the distal portion of the guide tube assembly 114, including the electrode tip assembly 116, will deflect to the left. The guide tube assembly 114 will form a curve with a circumference substantially equal to the distance "A" shown in FIG. 6, namely, the distance between the distal end 167 of the shaft 162 and the distal end of the electrode tip assembly 116.

FIGS. 7A and 7B show the resulting deflection of the distal region of the guide tube assembly 114 when it is steered to the left and right respectively. When steered to the left (FIG. 7A), the length of the left steering wire 58 is necessarily shortened, due to the action of the steering assembly, and therefore imparts a generally left deflection on the guide tube assembly 114. Since there is nothing interfering with the deflection of the sheath 166, the guide tube assembly 114 bends to the left with a circumference substantially equal to the distance "A". In FIG. 7A, the fulcrum point of the bending moment is adjacent to the distal end 167 of the shaft 162, therefore, the portion of the guide tube assembly 114 that is distal to the distal end 167 of the shaft 162 can deflect when the left steering wire 58 is pulled. Thus, it can be appreciated that the steering mechanism 18, center support wire 178, and left steering wire 58 are arranged to selectively bend the guide tube assembly 114 in a first direction into a first configuration, as illustrated in FIG. 7A.

When pulled to the right (FIG. 7B), the length of the right steering wire 56 is necessarily shortened, due to the action of the steering assembly, and therefore imparts a generally right deflection on the guide tube assembly 114. The second stiffening member 168 is a substantially rigid member, similar in construction to the center support wire 178, and is attached to the inside surface 165 of the sheath 166. Due to the second stiffening member 168, the portion of the sheath 166 that is adjacent to the second stiffening member 168 cannot compress. Therefore, the adjacent portion of the center support wire 178 and the adjacent portion of the guide tube assembly 114 cannot deflect. The fulcrum of the bending moment is translated to the distal end 172 of the second stiffening member 168, and only the portion of the guide tube assembly 114 that is distal to the second stiffening member 168 bends. The resulting curve has a circumference substantially equal to the distance "B", namely, the distance between the distal end 172 of the second stiffening member 168, and the distal end of the electrode tip assembly 116. Thus, it can be appreciated that the steering assembly 18, center support wire 178, right steering wire 56, and second stiffening member 168 are arranged to selectively bend the guide tube assembly 114 in a second direction into a second configuration, as illustrated in FIG. 7B.

FIGS. 8–9B show a further alternate embodiment of a guide tube assembly 214 constructed in accordance with the present invention. The guide tube assembly 214 further utilizes several stiffening members that are placed along the length of the guide tube assembly to vary the bending properties of the device. The configuration of the stiffening members enables the distal region of the guide tube assembly 214 to assume two different shapes when steered.

While generally similar in construction to the previously described guide tube assemblies, the guide tube assembly 214 includes a second stiffening member 294 and a third stiffening member 295 in addition to a shaft 262 (which functions as a first stiffening member). A center support wire 278 extends from the distal end of the shaft 262, which is similar in construction to the center support wire 78 described previously. Both the second and third stiffening members are preferably flat metal wires similar in construction to the center support wire 278. The second stiffening member 294 is disposed on the left side of the center support wire 278 and is substantially aligned with the left steering wire 58. The second stiffening member 294 is affixed to the center support wire 178 by a spot weld 272.

The third stiffening member 295 is disposed on the right side of the center support wire 278 and is substantially aligned with the right steering wire 56. The third stiffening member 295 is not affixed to the center support wire 278 but is instead affixed to an inside surface 265 of the sheath 266 and to a metal support ring 270 that wraps around the inside surface 265 of the sheath 266 at a point just proximal to the third stiffening member 295. An adhesive or other bonding agent 273 is used to affix the third stiffening member 295 to the sheath 266 and the support ring 270.

With the arrangement shown in FIG. 8, the distal portion of the guide tube assembly 214, and more specifically, the electrode tip assembly 216, assumes a first shape when steered to the left and another shape when steered to the right. While the previously described guide tube assemblies 14 and 114 form bending shapes with substantially circular profiles and different circumferences, the guide tube assembly 214 forms a substantially circular profile when bent in one direction and a partially curved—partially straight profile when bent in the other direction.

In operation, when the left steering wire 58 is pulled, i.e. by activation of the steering assembly 18, the center support wire 278 and therefore the distal portion of the guide tube assembly 214, including the electrode assembly 216, will deflect to the left. In this state, the guide tube assembly 214 will bend to the left, but its distal portion will maintain a substantially straight profile, due to the presence of the second stiffening member 294. The added rigidity of the second stiffening member 294 prevents the distal portion of the guide tube assembly 214 that is adjacent to the second stiffening member 294 from bending. When the guide tube assembly 214 is steered to the right, however, the assembly assumes a shape with a substantially circular profile lacking any straight portion.

FIGS. 9A and 9B show the resulting deflection of the distal region of the guide tube assembly 214 when it is steered to the left and right respectively. When steered to the left (FIG. 9A), the length of the left steering wire 58 is necessarily shortened, due to the action of the steering assembly 18, and therefore imparts a generally left deflection on the guide tube assembly 214. Since the second stiffening member 294 prevents the adjacent portion of the guide tube assembly 214 from deflecting, only the portion of the guide tube assembly 214 that is proximal to the second stiffening member will bend. In FIG. 9A, the fulcrum point of the bending moment is adjacent to the distal end 267 of the shaft 262. The orientation of the second stiffening member 294 prevents the entire portion of the guide tube assembly 214 from bending when the left steering wire 58 is pulled. The resulting shape of the guide tube assembly 214 when the left steering wire 58 is pulled includes a curved region and a substantially straight portion extending from the distal end of the curved region. Thus, it can be appreciated that the steering assembly 18, center support wire 278, left steering wire 58, and second stiffening member 294 are arranged to selectively bend the guide tube assembly 114 in a first direction into a first configuration, as illustrated in FIG. 9A.

When pulled to the right (FIG. 9B), the length of the right steering wire 56 is necessarily shortened, due to the action of the steering assembly, and therefore imparts a generally right deflection on the guide tube assembly 214. The third stiffening member 295 is a substantially rigid member, similar in construction to the center support wire 178 described above, and is attached to the inside surface 265 of the sheath 266. The portion of the sheath 266 that is adjacent to the third stiffening member 295 cannot compress due to the presence of the third stiffening member 295. The adjacent portion of the center support wire 278 and the adjacent portion of the guide tube assembly 214 cannot deflect. The fulcrum of the bending moment is therefore translated to the distal end 292 of the third stiffening member 295, and only the portion of the guide tube assembly 214 that is distal to the third stiffening member 295 can deflect. The resulting curve has a circumference substantially equal to the distance between the distal end 292 of the third stiffening member 295, and the distal end of the electrode tip assembly 216. Thus, it can be appreciated that the steering assembly 18, center support wire 278, right steering wire 58, and third stiffening member 295 are arranged to selectively bend the guide tube assembly 114 in a first direction into a first configuration, as illustrated in FIG. 9B.

Various other specific embodiments of a steerable medical device constructed in accordance with the present invention are contemplated by the present invention. For instance, various arrangements of the several stiffening members can be placed at different positions along the length of the guide tube assembly in order to create a steering catheter that has bending shapes customized for various procedures. Larger or smaller circumferences can be obtained by varying the length of the several stiffening members and by varying the way that the various stiffening members are connected to the internal components of the guide tube assembly. Materials with varying stiffness can be utilized to further modify the shape of the resulting bending curves that the guide tube assembly assumes.

Although the invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A steerable medical device, comprising:
    an elongated tubular body;
    a center support wire extending along the tubular body;
    a first stiffening member extending along the tubular body;
    a second stiffening member extending along the tubular body distally of the first stiffening member, wherein the second stiffening member is disposed on one side of the center support wire;
    a first steering wire having a distal end coupled to the center support wire, wherein operation of the first steering wire bends the center support wire in a first direction to create a bending moment having a fulcrum point adjacent a distal end of the second stiffening member; and
    a second steering wire having a distal end coupled to the center support wire, wherein operation of the second steering wire bends the center support wire in a second direction to create a bending moment having a fulcrum point adjacent a distal end of the first stiffening member, wherein the second direction is non-perpendicular to the first direction.

2. The steerable medical device of claim 1, wherein the first and second steering wires are coupled to the center support wire distal to the second stiffening member.

3. The steerable medical device of claim 1, wherein the first and second steering wires are coupled to a distal end of the center support wire.

4. The steerable medical device of claim 1, wherein the center support wire has opposing first and second sides.

5. The steerable medical device of claim 1, wherein the first stiffening member extends from a proximal end on the tubular body to a first intermediate point on the tubular body, and the second stiffening member extends from a second intermediate point on the tubular body to a third intermediate point on the tubular body.

6. The steerable medical device of claim 5, wherein the second intermediate point is distal to the first intermediate point.

7. The steerable medical device of claim 5, wherein the second intermediate point is the distal end of the first stiffening member.

8. The steerable medical device of claim 1, wherein the first stiffening member extends from a first intermediate point on the tubular body to a second intermediate point on the tubular body, and the second stiffening member extends from a third intermediate point on the tubular body to a fourth intermediate point on the tubular body.

9. The steerable medical device of claim 1, wherein the center support wire extends from the first stiffening member.

10. The steerable medical device of claim 1, wherein the first and second stiffening members are compression coils.

11. The steerable medical device of claim 1, wherein the first stiffening member is a compression coil, and the second stiffening member has a substantially flat profile.

12. The steerable medical device of claim 1, herein the first and second stiffening members have a substantially flat profile.

13. The steerable medical device of claim 1, wherein the second stiffening member is a compression coil.

14. The steerable medical device of claim 1, wherein the second stiffening member has a substantially flat profile.

15. The steerable medical device of claim 1, further comprising a guide tube connector positioned intermediate to and connected to the first and second stiffening members.

16. The steerable medical device of claim 1, wherein the second stiffening member is attached to the center support wire.

17. The steerable medical device of claim 1, wherein the elongated tubular body comprises a flexible sheath, and the second stiffening member is attached to the inside surface of the sheath.

18. The steerable medical device of claim 1, further comprising a third stiffening member extending along the tubular body distally of the second stiffening member, wherein the third stiffening member is disposed on a side of the center support wire opposite to the one side along which the second stiffening member is disposed, wherein the second steering wire is coupled to the center support wire at a point distal to the second stiffening member.

19. The steerable medical device of claim 1, wherein the first and second steering wires are operable for selectively bending the tubular body in a first direction into a first configuration and in a second direction into a second configuration.

20. The steerable medical device of claim 19, wherein the first configuration is a function of the length of the first stiffening member, and the second configuration is a function of the length of the first and second stiffening members.

21. The steerable medical device of claim 1, further comprising a steering assembly, wherein the first and second steering wires are coupled to the steering assembly.

22. The steerable medical device of claim 21, wherein the steering assembly comprises a rotatable cam, and wherein the distal end of each of the steering wires is attached to the cam.

23. The steerable medical device of claim 1, wherein the second steering wire extends through the first stiffening member, and the first steering wire extends through the first and second stiffening members.

24. The steerable medical device of claim 1, wherein the bending moment associated with an operation of the first steering wire is created by a distal end of the second stiffening member, and the bending moment associated with an operation of the second steering wire is created by the distal end of a first stiffening member.

25. The steerable medical device of claim 1, wherein the elongated tubular body is a catheter body.

26. A steerable medical device, comprising:
 an elongated tubular body;
 a substantially flat center support wire extending along the tubular body, the center support wire having first and second opposing surfaces;
 a first stiffening member extending distally to a first intermediate point on the tubular body;
 a second stiffening member extending from a second intermediate point on the tubular body to a third intermediate point on the tubular body, wherein the second stiffening member is disposed along one of the opposing surfaces of the center support wire;
 a first steering wire having a distal end coupled to the center support wire at a point distal to. the third intermediate point, wherein operation of the first steering wire bends the center support wire towards the second stiffening member in a first direction to create a bending moment having a fulcrum point adjacent the third intermediate point; and
 a second steering wire having a distal end coupled to the center support wire at a point distal to the first intermediate point, wherein operation of the second steering wire bends the center support wire away from the second stiffening member in a second direction to create a bending moment having a fulcrum point proximal to the second intermediate point, wherein the second direction is non-perpendicular to the first direction.

27. The steerable medical device of claim 1, wherein the second intermediate point is distal to the first intermediate point.

28. The steerable medical device of claim 1, wherein the second intermediate point is the distal end of the first stiffening member.

29. The steerable medical device of claim 1, wherein the first and second stiffening members are compression coils.

30. The steerable medical device of claim 1, further comprising a guide tube connector positioned intermediate to and connected to the first and second stiffening members.

31. The steerable medical device of claim 1, wherein the center support wire extends from the distal end of the first stiffening member.

32. The steerable medical device of claim 1, further comprising a steering assembly, wherein the first and second steering wires have proximal ends coupled to the steering assembly for selectively bending the tubular body in the first direction into a first configuration and in the second direction into a second different configuration.

33. The steerable medical device of claim 7, wherein the first configuration is a function of the length of the first stiffening member and the second configuration is a function of the length of the first and second stiffening members.

34. The steerable medical device of claim 7, wherein the steering assembly comprises a rotatable cam and wherein each of the steering wires is attached to the cam.

35. The steerable medical device of claim 1, wherein the second steering wire extends through the first stiffening member, and wherein the first steering wire extends through the first and second stiffening members.

36. The steerable medical device of claim 1, wherein the first stiffening member extends distally from a proximal end of the tubular body.

37. The steerable medical device of claim 1, wherein the first and second steering wires extend along the opposing surfaces of the center support wire.

38. The steerable medical device of claim 1, wherein the distal ends of the first and second steering wires are coupled to a distal end of the center support wire.

39. The steerable medical device of claim 1, wherein the second fulcrum point is adjacent the first intermediate point.

40. The steerable medical device of claim 1, wherein the second stiffening member is connected to the center support wire.

41. The steerable medical device of claim 1, wherein the first stiffening member is a compression coil, and the second stiffening member has a substantially flat profile.

42. The steerable medical device of claim 1, wherein the second stiffening member is a compression coil.

43. The steerable medical device of claim 1, wherein the second stiffening member has a substantially flat profile.

44. The steerable medical device of claim 1, wherein the elongated tubular body comprises a flexible sheath, and the second stiffening member is attached to the inside surface of the sheath.

45. The steerable medical device of claim 1, further comprising a third stiffening member extending from a fourth intermediate point on the tubular body to a fifth intermediate point on the tubular body, wherein the third stiffening member is disposed along a surface of the center support wire opposite to the one of the opposing surfaces along which the second stiffening member is disposed.

46. The steerable medical device of claim 1, wherein the elongated tubular body is a catheter body.

47. A steerable medical device, comprising:

an elongated tubular body with a proximal end and a distal end;

means for selectively bending the tubular body in a first direction into a first configuration;

means for selectively bending the tubular body in a second direction into a second configuration that is different from the first configuration, the second direction being non-perpendicular to the first direction.

48. The steerable medical device of claim 47, wherein the elongated tubular body is a catheter body.

* * * * *